(12) United States Patent
Killingbeck

(10) Patent No.: US 7,124,652 B2
(45) Date of Patent: Oct. 24, 2006

(54) METHODS FOR PROMOTING SLEEP SYSTEMS

(75) Inventor: Larry W. Killingbeck, Littleton, CO (US)

(73) Assignee: Denver Mattress Co., LLC, Lakewood, CO (US)

( * ) Notice: Subject to any disclaimer, the term of this patent is extended or adjusted under 35 U.S.C. 154(b) by 0 days.

(21) Appl. No.: 11/294,923

(22) Filed: Dec. 5, 2005

(65) Prior Publication Data

US 2006/0081075 A1     Apr. 20, 2006

Related U.S. Application Data

(62) Division of application No. 10/436,544, filed on May 12, 2003, now Pat. No. 6,997,070.

(60) Provisional application No. 60/429,989, filed on Nov. 27, 2002.

(51) Int. Cl.
*A47C 31/12* (2006.01)
*G01M 19/00* (2006.01)

(52) U.S. Cl. .................................................. 73/865.9

(58) Field of Classification Search .............. 73/865.9, 73/9, 172; 5/694
See application file for complete search history.

(56) References Cited

U.S. PATENT DOCUMENTS

| | | | | |
|---|---|---|---|---|
| 2,327,829 A | * | 8/1943 | Sternberg et al. | 73/172 X |
| 2,378,039 A | * | 6/1945 | Schenker | 73/172 |
| 2,666,327 A | * | 1/1954 | Taylor | 73/172 |
| 3,100,992 A | * | 8/1963 | Davis | 73/172 |
| 3,334,517 A | * | 8/1967 | Janapol | 73/865.9 X |
| 4,424,710 A | * | 1/1984 | Von Nortwick, II | 73/172 |
| 5,970,789 A | * | 10/1999 | Meyer et al. | 73/172 |
| 6,220,088 B1 | * | 4/2001 | Scales et al. | 73/172 |
| 6,561,047 B1 | * | 5/2003 | Gladney et al. | 73/865.3 |
| 6,721,980 B1 | * | 4/2004 | Price et al. | 73/172 X |

* cited by examiner

*Primary Examiner*—Thomas P. Noland
(74) *Attorney, Agent, or Firm*—Townsend and Townsend and Crew LLP

(57) ABSTRACT

A method for selecting a sleep system comprises positioning a person on a mattress in a lying position. One of the person's arms extends generally perpendicular to the person's torso. A first pillow is positioned underneath the person's head, and a force is applied to the person's arm in a direction generally toward the person's feet. An amount of resistive force supplied by the person's arm is estimated and used to determine whether the proper combination of mattress and pillow is achieved.

1 Claim, 5 Drawing Sheets

METHODS FOR PROMOTING SLEEP SYSTEMS

CROSS REFERENCES TO RELATED APPLICATIONS

This application is a continuation in part and claims the benefit of U.S. Provisional Patent Application No. 60/429,989, filed Nov. 27, 2002, the complete disclosure of which is herein incorporated by reference.

BACKGROUND OF THE INVENTION

This invention relates generally to the field of sleep systems, and in particular to sleep system that comprise both sleep surfaces, such as mattresses, and pillows. More specifically, the invention relates to methods for determining appropriate combinations of mattresses and pillows. In certain aspects, such a determination may be used to enhance the sales of mattresses and pillows, alone or in combination.

Finding the correct mattress can be a difficult task. Within the United States there are literally hundreds of makes and models of mattresses, such as firm mattress, plush mattresses, and the like. Selecting a mattress that will provide an appropriate degree of comfort and/or support to meet a person's needs can be especially challenging.

The use of an appropriate pillow can also be a factor in determining the level of comfort and/or support. For example, if the pillow is too high, too firm, or the like, the user's comfort level and/or the amount of support provided to the user may be seriously compromised.

Importantly, the user's comfort and the amount of support can also be affected by the combination of both the pillow and the mattress. For example, depending on the type of mattress that is selected, a different type of pillow may be needed to provide the appropriate support and/or comfort level. At present, it is believed that no suitable techniques exist for the determining an appropriate sleep system that includes the combination of a pillow and a mattress.

BRIEF SUMMARY OF THE INVENTION

In one embodiment, a method is provided for selecting a sleep system. According to the method, a person is instructed to lie on a mattress, either on the person's side, back or stomach. A pillow is positioned underneath the person's head and the person is instructed to extend one of his arms generally perpendicular to his torso. A force is then applied to the person's arm in a direction generally toward the person's feet. While applying the force, an amount of resistance supplied by the person's arm is estimated.

The pillow may then be removed and replaced with another pillow and the process repeated. A comparison may then be made between the resistive force supplied by the person then lying on the first pillow with the resistive force applied by the person when lying on the second pillow. A recommendation may then be made to use the pillow that is associated with the test for which the person's arm generates the greatest amount of resistive force. By determining which test produces the most amount of resistance, an assumption may be made that this pillow in combination with the selected mattress places the person's spine in the most neutral position. In this way, the person's muscles are permitted to relax, resulting in fewer pressure points and less muscle soreness when lying on the sleep system. A generally neutral spinal alignment also maximizes the person's comfort/support when lying on the mattress. This strength resistance test may be repeated using additional pillows until the preferred pillow is determined.

Such a process may also be used to select a preferred mattress. For example, a person may be instructed to lie on a first mattress while performing the strength resistance test. The person may then lie on a second mattress while the strength resistance test is repeated. Based at least in part on which test results in the most resistive force by the person, that mattress may be selected as the preferred mattress. This process may be iteratively repeated for several mattresses.

The amount of resistive force supplied by the person's arm may be based on a variety of factors. Such factors may include the height of the pillow, the firmness of the pillow, the density of the pillow, the firmness of the mattress, and the like. By selecting the appropriate combination of mattress and pillow, a sleep system which is best suited for a person's particular needs may be determined. Other factors that may be considered in selected the preferred mattress and/or pillow include how well the person's spine is aligned based on a visual inspection, how comfortable the person feels when lying on the mattress and pillow, and the like.

The invention also provides a tailored sleep system that comprises a mattress and a pillow. The pillow and the mattress are selected to maximize the amount of resistance to a force applied to a user's arm when performing a strength resistance test. During such a test, the user lays on a mattress on the person's back, side or stomach, with one of the user's arms extending generally perpendicular to the user's torso. Further, the pillow is positioned underneath the user's head, and the force is applied to the user's arm in a direction generally toward the user's feet.

DETAILED DESCRIPTION OF THE INVENTION

Figure 1:
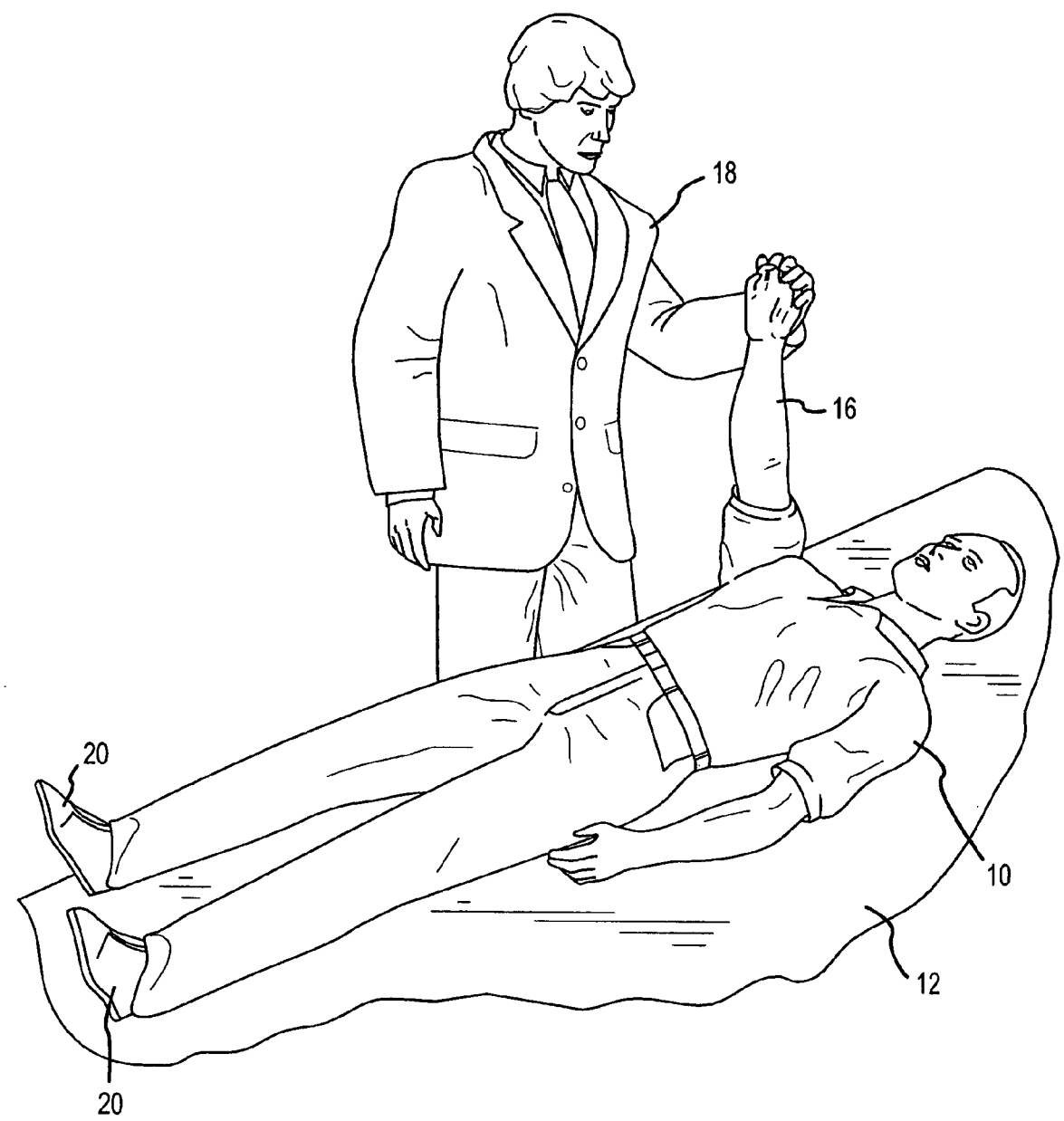
FIG. 1 illustrates a strength resistance test performed on a mattress without a pillow according to the invention.

The invention provides exemplary techniques for determining an appropriate sleep system. Such sleep systems typically comprise a sleep surface, such as a mattress, and one or more pillows. The techniques of the invention are suited for determining appropriate combinations of sleep surfaces and pillows that assist in providing a neutral spinal alignment when the person is lying down on the sleep system. When the person's spine is in a neutral alignment, the amount of comfort/support that the person experiences is maximized. The techniques may also be used to select a preferred mattress.

The techniques of the invention may utilize a strength resistance test to determine if the person's spine is in proper alignment. When such is the case, the person's muscles may easily resist applied pressure. However, if the spine is out of the neutral position by even a small amount, a significant reduction in resistive force may be detected.

The strength resistance tests of the invention are designed to correlate sleep surfaces with pillows, and in some cases simply to select an appropriate sleep surface. Such sleep surfaces may include, for example, mattresses, including spring mattresses, solid mattresses, padded surfaces, firm surfaces, and the like. Further, the pillows may be stuffed with a filling, inflatable, or the like.

As the person's spine is placed in a generally neutral position, the person's muscles are permitted to relax, resulting in fewer pressure points and muscle soreness. Presumably, this will lead to a better night's rest and less partner disturbance. As such, the neutral position maximizes the amount of comfort/support experienced by the user.

Hence, such a test may be used to determine an appropriate sleep surface and pillow that is best suited for a person's needs. To perform the sleep resistance test, the person is instructed to lie down with one arm extended generally perpendicular to the body. The person may lie on his back, side or stomach. Another person gently pushes the person's arm toward their feet with a firm, smooth motion. The most appropriate combination of sleep surface or sleep surface and pillow results when the person feels the strongest and most easily resists the applied force. Other factors may also be used in determining the appropriate sleep surface and pillow, including how well the spine is aligned based on a visual inspection, how comfortable the user feels and the like. Such additional factors may be used, for example, in cases where two tests produce similar resistances.

To begin the process, in one embodiment, the person may first be instructed to select a preferred mattress. However, it will be appreciated that the person may alternatively wish to first select the desired pillow. The particular mattress may be selected based on the comfort level and support that best fits the person's needs. This determination may be based on whether the person's spine is in alignment when lying on the sleep system. Also, a strength resistance test may be used to determine the preferred mattress. After the person has selected the mattress, they are then fitted with a pillow to insure the sleep system as a whole fits the person's needs. In many cases, a person's old pillow will be unsuitable for a new plusher mattress. Hence, even if the person was previously satisfied with their pillow, when changing to a new mattress the old pillow may serve to place the spine out of alignment. Hence, a number of pillows may be required to determine the appropriate sleep system.

Using a variety of pillows, the person's arm is pushed toward her feet to determine the resistive force. The pillow that is associated with the greatest resistive force may be recommended based on the assumption that this pillow provides the most neutral position, i.e., where the spine is in alignment, in combination with the chosen mattress.

FIG. 1 illustrates one example of a strength resistance test that may be used in selecting a mattress, or a baseline strength test for comparison with the results of other tests. Initially, a person 10 is instructed to lie on a sleep surface 12, such as a mattress. As shown, person 10 is lying on his back. However, other orientations may also be used, such as by lying on the person's side or stomach. This particular test is performed without a pillow under the person's head. The person 12 lies flat on the sleep surface 12 with his arm 16 generally perpendicular to the sleep surface 12, with the palm positioned towards the person's feet 20. The tester 18 instructs the person 10 to try to maintain his arm 16 in the vertical position while the tester 18 pushes the person's arm 16 toward his feet 20. During the test, the tester 18 and/or the person 10 notes the amount of resistance provided by the person 10. 1241 The amount of measured resistance may be used for a variety of purposes. For example, it may be used as a baseline measurement for subsequent tests as described hereinafter. Alternatively, it may be used when fitting a person for a particular sleep surface. For example, this same test may be repeated while lying on another sleep surface and the two measurements compared to determine which sleep surface is more suitable to the user. This decision may be based on the sleep surface that is associated with the greatest amount of measured resistance.

Figure 2:
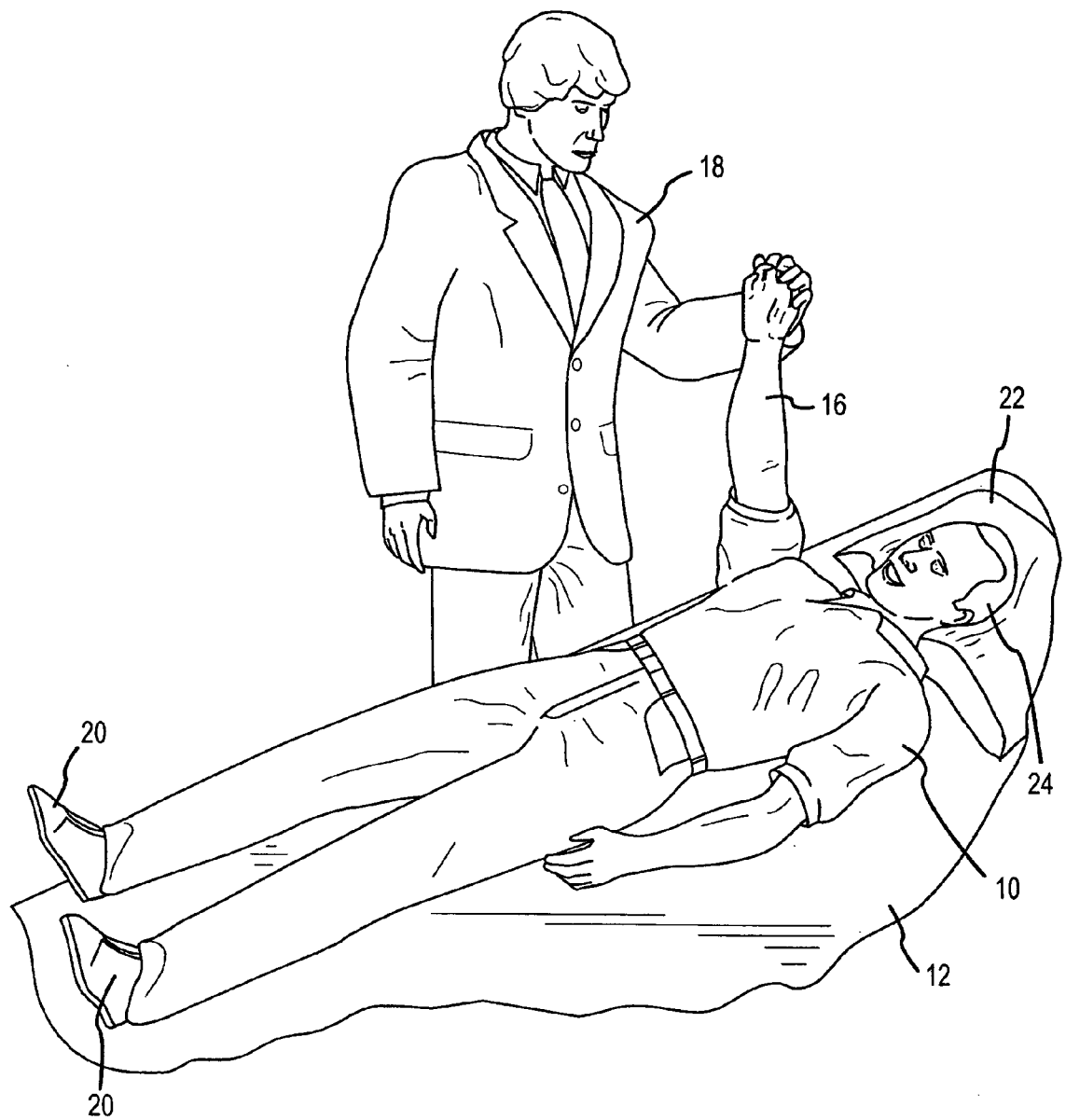
FIG. 2 illustrates a strength resistance test performed on a mattress with a pillow and while the user is on his back according to the invention.

Although shown without a pillow, the base line test may also be made with a pillow underneath the person's head. Once a baseline resistance measurement is made by the tester, a pillow 22 (or another pillow) is placed underneath the person's head 24, and the test is repeated as shown in FIG. 2. The resistance generated by the person 10 is measured by the tester 18 and then compared with the baseline measurement. A decision as to which pillow to select may then be made based on the one that was used with the test measuring the greatest amount of resistance. This test may be repeated as many times as needed with different pillows and/or mattresses until the tester 18 and/or person 10 has decided which mattress/pillow combination produces the greatest amount of resistance during the test. Other factors that may be used in selecting the mattress and/or pillow include how well the person's spine is aligned based on a visual observation, the amount of comfort experienced by the person 10, and the like.

Figure 3:
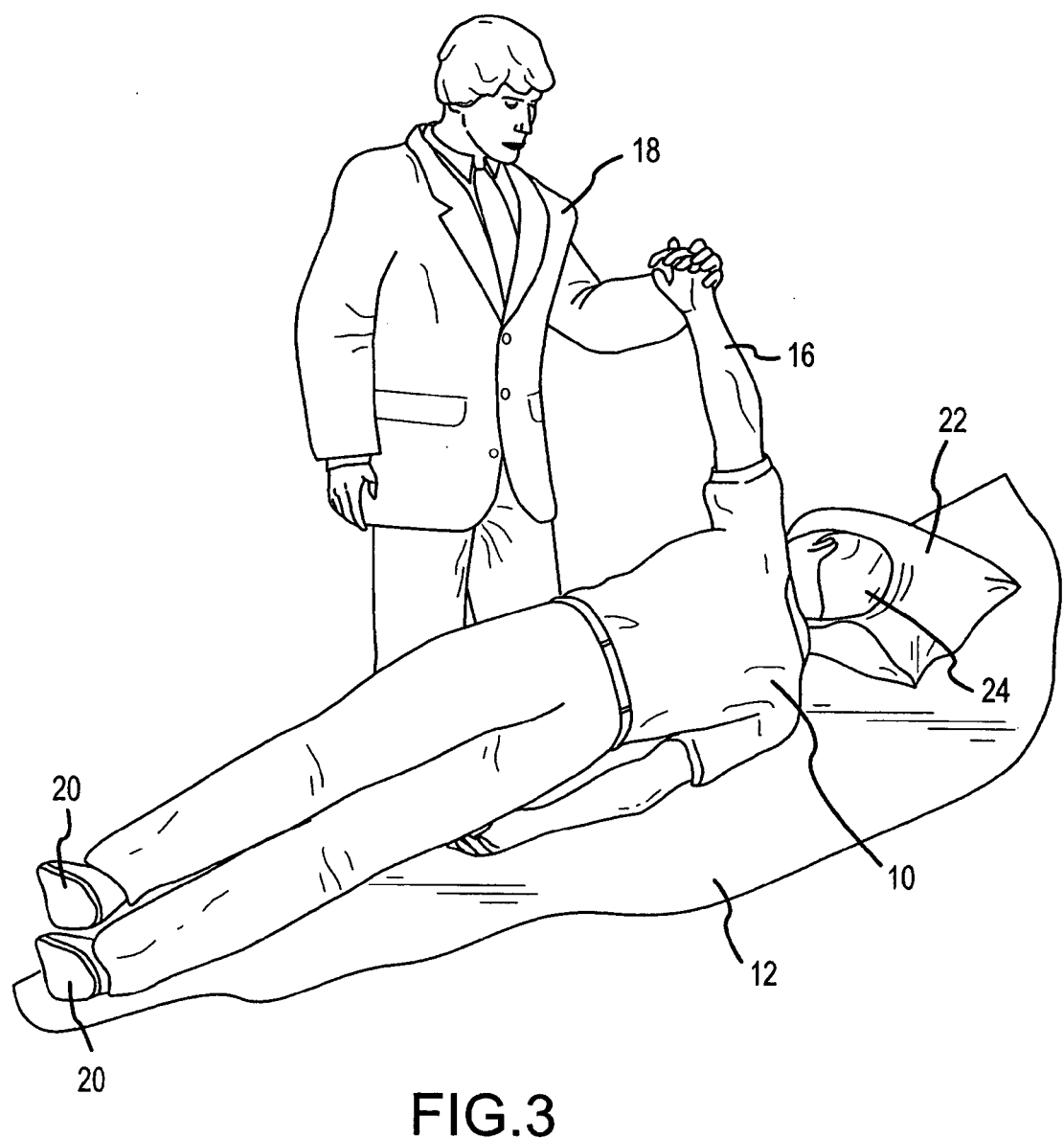
FIG. 3 illustrates a strength resistance test performed on a mattress with a pillow and while the user is on his side according to the invention.

In addition to lying on the person's back, other orientations may be used as well. For example, as shown in FIG. 3, person 10 may lie on his side with his arm 16 pointing upward and the palm generally facing the person's feet 20. Alternatively, the person's arm 16 may be positioned generally horizontal while being perpendicular to his body, with the person's palm facing the feet 12. The tester 18 performs the strength resistance test by pushing the arm 16 generally toward the feet 20 while noting the amount of resistance provided by the person 10 in a manner similar to that previously described. Such a test may be particularly useful for people who tend to generally sleep on their side.

Figure 4:
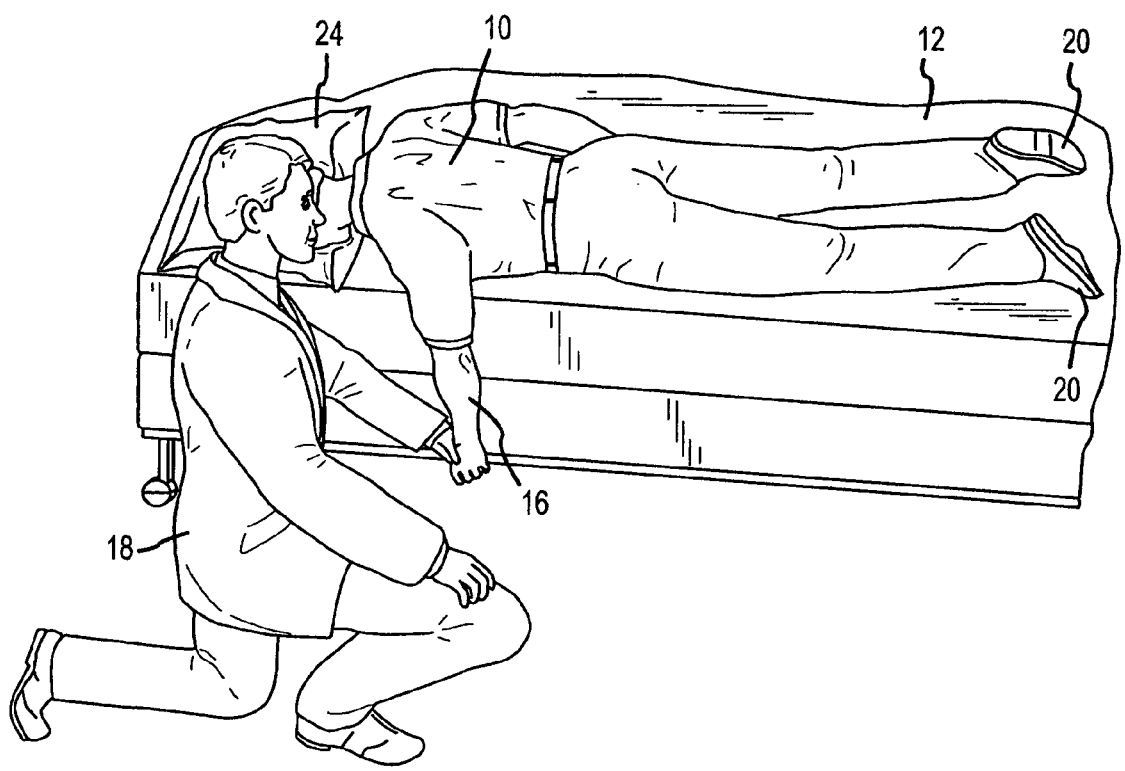
FIG. 4 illustrates a strength resistance test performed on a mattress with a pillow and while the user is on his stomach according to the invention.

FIG. 4 illustrates the strength resistance test when the person 10 is lying on his stomach. The person's arm 16 is positioned downward toward the floor, with the palm facing the feet 20. Tester 18 presses the person's arm 16 toward the feet while the person 10 resists the force. This test may then be performed on other sleep surfaces and/or pillows to select the appropriate sleep surface and/or pillow in a manner to that previously described. Such a test is particularly useful for individuals who primarily sleep on their stomachs.

Figure 5:
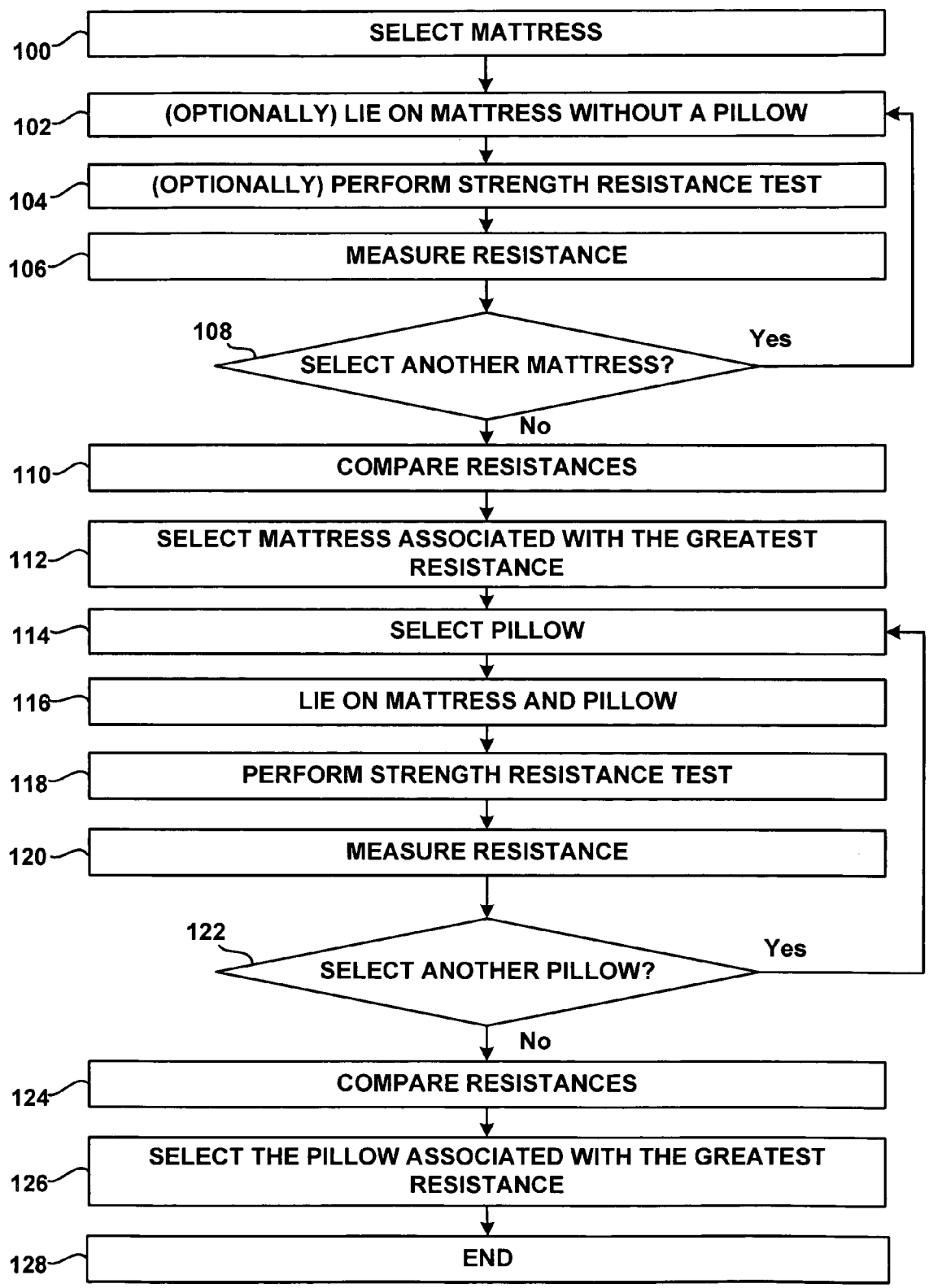
FIG. 5 illustrates one method for selecting a mattress or a mattress in combination with a pillow according to the invention.

Referring now to FIG. 5, one method for selecting preferred sleep surfaces and pillows will be described. Initially, the user selects a sleep surface, such as a mattress as illustrated in step 100. Optionally, the user may lay on the mattress without a pillow as shown in step 102. This may be the case, for example, when the user is attempting to select an appropriate mattress. As another example, the user may lay on the mattress without the pillow to perform a baseline strength resistance test that is to be compared with other tests where a pillow is used.

A strength resistance test is then performed on the user as shown in step 104, and the amount of resistance produced by the user when lying down is measured as shown in step 106. The user may then select another mattress as shown in step 108. Steps 102, 104 and 106 are then repeated for the second mattress. This process may be repeated for as many mattresses as the user wishes to test.

At step 110, the resistances produced during each of the tests are compared, and the mattress that is associated with the greatest resistance may be chosen as shown in step 112. In some cases, the above process make be performed in an iterative process. For example, the first two mattresses may be tested and the most preferred one selected. The test may then be repeated using mattresses selected from the first test with another mattress.

With a mattress selected, the user may proceed to associate a preferred pillow with the mattress. As shown in step 114, the user selects a pillow for the first test. The user lies on the mattress and the pillow (see step 116) in a familiar sleeping position, such as on the back, front or side. A strength test is then performed as shown in step 118, and the resistance produced by the user when lying down is measured in step 120. The user decides whether to selects another pillow in step 122 and, if so, steps 114, 116, 118 and 120 are repeated. With a desired number of tests have been performed, the resistances are compared in step 124 and the pillow that is associated with the greatest resistance is selected in step 126. As when selecting a mattress, the process of selecting the pillow can be an iterative process.

The invention has now been described in detail for purposes of clarity and understanding. However, it will be appreciated that certain changes and modifications may be practiced within the scope of the appended claims.

What is claimed is:

1. A method for selecting a mattress from a group of mattresses, the method comprising:

positioning a person on a first mattress in a lying position, with one of the person's arms extending generally perpendicular to the person's torso;

applying a force to the person's arm in a direction generally toward the person's feet;

estimating an amount of resistance to the force supplied by the person's arm.

positioning the person on a second mattress in a lying position, with one of the person's arms extending generally perpendicular to the person's torso;

applying a force to the person's arm in a direction generally toward the persons feet;

estimating an amount of resistance to the force supplied by the person's arm;

comparing the amount of resistance produced when lying on the first mattress with the amount of resistance produced when lying on the second mattress to determine which of the resistances were the greatest; and selecting the mattress that is associated with the greatest resistance.

* * * * *